(12) United States Patent
Hesse et al.

(10) Patent No.: US 6,372,926 B2
(45) Date of Patent: *Apr. 16, 2002

(54) 17-SIDE CHAIN ALKYNYL-AND 20-OXOPREGNA-DERIVATIVES OF VITAMIN D, METHODS FOR THEIR PRODUCTION AND PHARMACEUTICAL COMPOSITIONS THEREOF

(75) Inventors: Robert Henry Hesse, Winchester; Maurice Murdoch Pechet; Sundara Katugam Srinivasasetty Setty, both of Cambridge, all of MA (US)

(73) Assignee: Research Institute for Medicine and Chemistry, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,483
(22) PCT Filed: Dec. 23, 1996
(86) PCT No.: PCT/GB96/03218
  § 371 Date: Feb. 19, 1999
  § 102(e) Date: Feb. 19, 1999
(87) PCT Pub. No.: WO97/23453
  PCT Pub. Date: Jul. 3, 1997

(30) Foreign Application Priority Data

Dec. 21, 1997 (GB) .............................. 9526208

(51) Int. Cl.$^7$ ..................... C07C 401/00; A61K 31/593
(52) U.S. Cl. ..................... 552/653; 552/653; 514/167
(58) Field of Search ........................... 552/653; 514/167

(56) References Cited

U.S. PATENT DOCUMENTS 5,589,471 A * 12/1996 Hansen et al. ................ 14/167

FOREIGN PATENT DOCUMENTS

| EP | 0 639 377 A | 2/1995 |
| WO | 94 01398 A | 1/1994 |
| WO | 94 07852 A | 4/1994 |

OTHER PUBLICATIONS

Carter et al., Chemotherapy of cancer, Second edition, A Wiley Medical Publication, John Wiley & sons, 1981.*
Chemical Abstracts, vol. 091, No. 3, Jul. 16, 1979, Columbus Ohio, US; 020912. Ochi et al. "Vitamin D. Derivatives" p. 697; col. 2; Xp002029721, see abstract & JP 54 014 951—(Chugai Pharmaceutical Co., Ltd.; Japan) Feb. 3, 1979 & Database WPI Section Ch, Week 7911 Derwent Publications Ltd., London, GB; Class B01, AN 79–20584b & JP 54 014 951 A (Chugai Pharm Co Ltd), Feb. 3, 1979, see abstract.
Tetrahedron Letters, vol. 35, No. 15, Apr. 11, 1994, Oxford, GB, pp. 2295–2298, XP002029720 Perlman K L et al. : "20–Oxopregnacalciferols: vitamin D compounds that bind the progesterone receptor" cited int he application see p. 2296, line 10–line 15, see p. 2297; examples 3, 6, 9.
Chemical Abstracts, vol. 077, No. 3, Jul. 17, 1972 Columbus, Ohio, US; abstract No. 014045, Sharma S N et al.: "Antiimplantation effect of dihydrotachysterol and calciferol in rats" p. 28; clumn 1; XP002029722, see abstract & Curr. Sci., vol. 41, No. 5, 1972, pp. 181–182.

* cited by examiner

Primary Examiner—Sabiha Qazi
(74) Attorney, Agent, or Firm—Bacon & Thomas

(57) ABSTRACT

1-Hydroxy pregnacalciferol derivatives of formula (I) and their corresponding 5,6-trans isomers wherein $R^1$ is hydroxyl or lower alkoxy and $R^2$ is optionally hydroxylated or lower alkoxylated lower alkynyl or $R^1$ is $C(R^A)$ $(R^B)CH_3$ where $R^A$ is optionally hydroxylated or lower alkoxylated lower alkynyl and $R^B$ is hydroxyl or lower alkoxy or $R^A$ and $R^B$ together represent oxo and $R^2$ is hydrogen, hydroxyl or lower alkoxy, and $R^3$ and $R^4$ represent hydrogen atoms, exhibit anti-progesterone activity and may be useful as antineoplastic, antifertility, antiproliferative, immunosuppressive and/or antiinflammatory agents.

6 Claims, No Drawings

17-SIDE CHAIN ALKYNYL-AND 20-OXOPREGNA-DERIVATIVES OF VITAMIN D, METHODS FOR THEIR PRODUCTION AND PHARMACEUTICAL COMPOSITIONS THEREOF

This application is a 371 of PCT GB96/03218 Dec. 23, 1996.

This invention relates to new 1-hydroxy pregnacalciferol derivatives, more especially to 1-hydroxy pregnacalciferol derivatives having anti-progesterone activity.

Vitamin $D_3$ has long been known to play a key role in the metabolism of calcium. The discovery that the D vitamins undergo hydroxylation in vivo led to the synthesis of many analogues of vitamin D whose evaluation indicated that hydroxyl groups at the 1α-position and at either the 24R- or 25-position were essential for the compound or metabolite thereof to exhibit a substantial effect on calcium metabolism.

Subsequent work indicated that the natural metabolite 1α,25-dihydroxy vitamin $D_3$ exhibited cell modulating activity, including stimulation of cell maturation and differentiation, as well as immunosuppressive effects, and also exhibited an immunopotentiating effect, stimulating the production of bactericidal oxygen metabolites and the chemotactic response of leukocytes.

The therapeutic potential of 1α,25-hydroxy vitamin $D_3$ in these areas is, however, severely limited by its potent effect on calcium metabolism. Thus dosages at a level sufficient to elicit a desired cell modulating, immunosuppressive or immunopotentiating effect tend to lead to unacceptable hypercalcaemia. Considerable interest has therefore been shown in the synthesis of analogues having reduced effects on calcium metabolism but still exhibiting desired effects on cellular metabolism, e.g. as summarised in WO 95/16672.

DeLuca and coworkers (Tetrahedron Letters 35(15) (1994), pp. 2295–2298 and Program Abstracts, 77th Annual Meeting of the Endocrine Society (1995), Abstract No. P2-662, p.456) have reported that in their investigations of such vitamin D analogues they have tested various 20-oxopregnacalciferols and found them to be inactive as regards effect on calcium metabolism. Noting that these compounds shared some structural features with progesterone and aware of the development of compounds such as RU 486, a 19-nor steroid having the formula

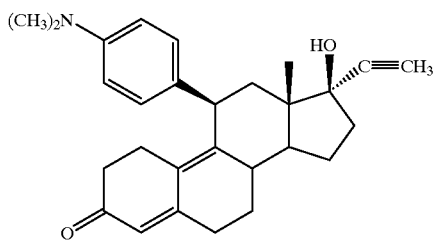

and exhibiting strong anti-progesterone and anti-glucocorticosteroid activities, they also tested these compounds for ability to bind to the progesterone receptor. 20-Oxopregnacalciferols, and to a lesser extent the 22-aldehyde and 22-hydroxy calciferols, were found to bind the progesterone receptor. Of "many other" vitamin D analogues tested no other showed significant binding activity. 1α-Hydroxy-20-oxopregna-calciferol and its corresponding 19-nor analogues are specifically stated not to have such binding effect.

In contrast to RU 486, 20-oxopregnacalciferol is said not to bind to the glutocorticoid receptor but has been found (Program Abstracts, 76th Annual Meeting of the Endocrine Society (1994), Abstract No. 1744, p. 636) to suppress in vitro growth of human breast cancer cells (T47D).

The present invention is based on the surprising finding that a number of 1-hydroxy pregnacalciferols, in complete contradiction to the findings of DeLuca et al., do in fact act as potent antagonists of progesterone activity, for example as evidenced by antifertility (e.g. contraceptive) activity, anti-progesterone assay and inhibition of growth of mammary cancer T47D and MCF-7 cell lines. Even more surprisingly, we have found that the anti-progesterone effects in respect of these 1-hydroxy compounds may exceed those of the corresponding 1-desoxy compounds.

Apart from the compound 1α-hydroxy-20-oxopregnacalciferol, insofar as it may have been disclosed by DeLuca et al., these 1-hydroxy pregnacalciferols and their O-protected derivatives are novel and constitute a feature of the invention.

Thus according to one aspect of the invention there are provided compounds of general formula (I):

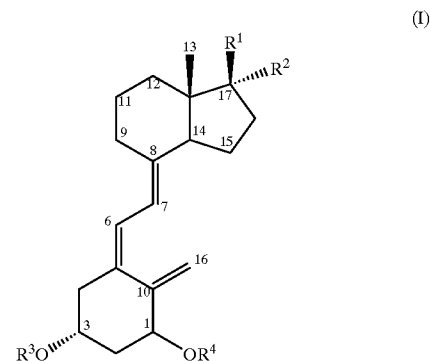

(wherein $R^1$ denotes an optionally protected hydroxyl group or a lower alkoxy group and $R^2$ denotes a lower alkynyl group optionally substituted by a hydroxyl, protected hydroxyl or lower alkoxy group; or $R^1$ denotes a group —$C(R^A)(R^B)CH_3$ wherein $R^A$ is a lower alkynyl group optionally substituted by a hydroxyl, protected hydroxyl or lower alkoxy group and $R^B$ is an optionally protected hydroxyl group or a lower alkoxy group, or $R^A$ and $R^B$ together represent an oxo group, and $R^2$ denotes a hydrogen atom, an optionally protected hydroxyl group or a lower alkoxy group; and $R^3$ and $R^4$, which may be the same or different, each denote a hydrogen atom or an O-protecting group) and the corresponding 5,6-trans (i.e. 5E-isomers) thereof, with the proviso that when $R^1$ denotes a group —$C(R^A)(R^B)CH_3$ wherein $R^A$ and $R^B$ together denote an oxo group and the group —$OR^4$ is in the α-configuration then $R^2$ is other than hydrogen.

Where any of $R^1$, $R^2$ and $R^B$ denote or contain lower alkoxy groups these may, for example, be $C_{1-6}$ alkoxy groups such as methoxy, ethoxy, propoxy and butoxy groups which, where appropriate, may be straight chain or branched.

Where $R^2$ or $R^A$ denotes a lower alkynyl group this may, for example, contain up to 6 carbon atoms, and may for example be an alk-l-yn-1-yl group such as ethynyl, 1-propynyl, 1-butynyl, 1-pentynyl or 1-hexynyl, or an ω-alkynyl group such as propargyl. Hydroxyl or lower alkoxy substituents may be present as in, for example, 3-hydroxypropynyl and 3-methoxypropynyl groups.

Where $R^3$ and $R^4$ represent O-protecting groups these may, for example, be cleavable O-protecting groups such as are commonly known in the art. Suitable groups include etherifying groups such as silyl groups (e.g. tri(lower alkyl) silyl groups such as trimethylsilyl, triethylsilyl, triisopropylsilyl or t-butyldimethylsilyl; tri(aryl)silyl groups such as triphenylsilyl; and mixed alkyl-arylsilyl groups); lower (e.g. $C_{1-6}$) alkyl groups optionally interrupted by an oxygen atom, such as methyl, methoxymethyl or methoxyethoxymethyl; and cyclic groups such as tetrahydropyranyl. Esterifying O-protecting groups include lower (e.g. $C_{1-6}$) alkanoyl such as acetyl, propionyl, isobutyryl or pivaloyl; aroyl (e.g. containing 7–15 carbon atoms) such as benzoyl or 4-phenylazobenzoyl; lower alkane sulphonyl such as (optionally halogenated) methane sulphonyl; and arene sulphonyl such as p-toluene sulphonyl.

O-protected derivatives are useful as intermediates in the preparation of active 1,3β-diols of formula (I). Additionally, where the O-protecting groups are metabolically labile in vivo, such ethers and esters of formula (I) may be useful directly in therapy.

5,6-Trans isomers of compounds of general formula (I) are useful as intermediates in the preparation of the corresponding 5,6-cis isomers, e.g. as described in greater detail hereinafter. Where $R^3$ and $R^4$ denote hydrogen atoms or metabolically labile groups such 5,6-trans isomers may, however, exhibit biological activity, although typically at a lower order of magnitude than corresponding 5,6-cis isomers, and thus may be useful in therapy.

The anti-progestational activity of both 1α-hydroxy-20-oxopregnacalciferol and active compounds of general formula (I) as defined above suggests their use as, for example, antiproliferative agents in, for example, the treatment and/or prevention of hormone responsive tumours or hyperplasias (such as breast, prostate or ovarian cancers, fibroids or endometriosis) or as suppressants of progesterone activity, for instance in oedema, acne, melasma or in fertility control (such as, for example, in inducing abortion or in contraception) in human or animal subjects. The invention accordingly embraces the use of these compounds both in treatment or prophylaxis of the above-mentioned conditions and in the manufacture of medicaments for such treatment or prophylaxis.

Whilst the antiproliferative effect of compounds according to the present invention is somewhat lower than that of 1α-hydroxy vitamin D analogues having cell modulating activity, for example as described in our International Patent Applications Nos. WO-A-9309093, WO-A-9426707, WO-A-9503273, WO-A-9516672 and WO-A-9525718, it is nonetheless significant and may be therapeutically useful since the compounds have an extremely low effect on calcium metabolisum and thus exhibit an advantageous therapeutic ratio. They may therefore find use in any of the applications described in the aforementioned WO-A-9309093, WO-A-9426707, WO-A-9503273, WO-A-9516672 and WO-A-9525718, the contents of which are incorporated herein by reference, for example as immunosuppressive and/or antiinflammatory agents.

It will be appreciated that compounds according to the invention may exhibit different activity profiles as regards their antineoplastic, antifertility, antiproliferative, immunosuppressive and/or antiinflammatory activity etc. Routine bioassay procedures may be used in known manner to select particular compounds most suited to particular therapeutic applications.

Active compounds according to the invention may be formulated for administration by any convenient route, e.g. orally (including sublingually), parenterally, rectally or by inhalation; pharmaceutical compositions so formulated comprise a feature of the invention.

Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally or intramuscularly.

Compositions for rectal administration may be formulated using a conventional suppository base such as cocoa butter or another glyceride.

Compositions for administration by inhalation are conveniently formulated for self-propelled delivery, e.g. in metered dose form, for example as a suspension in a propellant such as a halogenated hydrocarbon filled into an aerosol container provided with a metering dispense valve.

It may be advantageous to incorporate an antioxidant, for example ascorbic acid, butylated hydroxyanisole or hydroquinone in the compositions of the invention to enhance their storage life.

Where any of the above compositions are prepared in dosage unit form these may for example contain 0.5–2500 µg, e.g. 1–500 µg, of active compound according to the invention per unit dosage form. The compositions may if desired incorporate one or more further active ingredients, for example antiprogresterones such as RU 486, oestrogens or oestrogen antagonists.

A suitable daily dose of an active compound according to the invention may for example be in the range 1–5000 µg, e.g. 2–1000 µg, per day, depending on factors such as the severity of the condition being treated and the age, weight and condition of the subject.

Compounds according to the invention may be prepared by any convenient method, for example involving one or more of the following:

A) By isomerisation of a corresponding 5,6-trans compound, preferably in 1,3-di(O-protected) form. Isomerisation may be effected by, for example, treatment with iodine, with a disulphide or diselenide, or by irradiation with ultraviolet light, preferably in the presence of a triplet sensitiser. Such 5,6-trans compounds may themselves be prepared by oxidising a corresponding 1-desoxy-5,6-trans compound using a selenite ester or selenium dioxide or selenous acid in the presence of an alcohol, e.g. as described in GB-A-2038834, the contents of which are incorporated herein by reference. This process will generate the corresponding 1α- and 1β-hydroxy compounds as major and minor products respectively; these may readily be separated, e.g. by chromatography. The 1-desoxy-5,6-trans starting material may, if desired, be prepared in situ by isomerisation of the corresponding 1-desoxy-5,6-cis compound under the conditions of the oxidation.

B) By oxidising a compound (I) or corresponding 5,6-trans isomer in which $R^A$ and $R^B$ together denote an oxo group and $R^2$ denotes a hydrogen atom, preferably in 1,3-di(O-protected) form, or a corresponding 1-desoxy compound, to yield a compound in which $R^2$ denotes a hydroxyl group. Such oxidation may, for example, be effected using Barton/Gardner hydroxylation conditions, e.g. by passing air through a solution of the compound in one or more polar organic solvents, for example selected from cyclic ethers such as tetrahydrofuran and tertiary amides such as N,N-dimethylformamide, in the presence of a strong base, e.g. an alkali metal lower alkoxide such as potassium t-butoxide, preferably in the presence of the corresponding lower alkanol, e.g. t-butanol. The reaction is preferably carried out in the presence of a low valence phosphorus compound capable of reducing a hydroperoxide group to a hydroxyl group, for example a phosphine or phosphite, e.g. a tri(lower alkyl)phosphite such as triethylphosphite. Surprisingly it has been found that neither these severe oxidative conditions nor the reactive 17-hydroperoxide intermediate which is transiently formed react with or degrade the sensitive triene system present in the molecule. This unexpectedly effective and useful hydroxylation procedure accordingly constitutes a feature of the present invention. Where a 1-desoxy compound is prepared using this process it may subsequently be 1-hydroxylated, for example by oxidation using an appropriate selenium compound as described in (A) above to introduce a 1α-hydroxyl group.

C) By reaction of a preferably 1,3-di(O-protected) compound of formula (I) or corresponding 5,6-trans isomer in which $R^1$ and $R^2$ together or $R^A$ and $R^B$ together denote an oxo group with a lower alkynyl anion to yield a compound of formula (I) in which $R^1$ or $R^A$ is lower alkynyl and $R^2$ or $R^B$ is hydroxy. The lower alkynyl anion may be added in the form of a salt (e.g. an alkali metal salt such as a lithium salt) of the appropriate lower alkyne, if desired in the form of a complex with an appropriate material, for example a diamine, e.g. a lower alkylenediamine such as ethylenediamine, 1,2-diaminopropane or 1,3-diaminopropane, or it may be generated, if desired in situ, by treatment of the corresponding lower alkyne with a strong base such as sodium amide, lithium diisopropylamide or n-butyllithium. Alternatively the anion may be generated in situ from a corresponding silylated lower alkyne by reaction with a source of fluoride ion, for example anhydrous quaternary ammonium fluoride such as tetrabutylammonium fluoride. If this reaction is performed on a compound (I) in which $R^A$ and $R^B$ together denote an oxo group and $R^2$ denotes a hydroxyl group (e.g. prepared as in (B) above), this hydroxyl group will be correspondingly silylated during the course of the reaction. If the protecting groups are appropriately selected, e.g. if the 1- and 3-positions are protected as triisopropylsilyloxy groups and the $R^2$ hydroxy group as trimethylsilyloxy, this latter group may be selective cleaved, for example by mild acid hydrolysis, e.g. using acetic acid or dilute hydrochloric acid.

D) By alkylating a preferably 1,3-di(O-protected) compound (I) or corresponding 5,6-trans isomer in which $R^1$, $R^2$ or $R^B$ denotes a hydroxyl group to generate a corresponding compound in which $R^1$, $R^2$ or $R^B$ denotes a lower alkoxy group. Such alkylation may conveniently be effected by reaction with an alkylating agent such as a lower alkyl sulphonate or halide (e.g. chloride, bromide or, more preferably, iodide) in the presence of a base such as a metal hydride, e.g. an alkali metal hydride such as sodium or potassium hydride.

It will be appreciated that any of the above steps may be followed by removal of any O-protecting groups as necessary and/or desired, and that where more than one of the above steps is employed they may be used in any appropriate order.

In general, O-protecting groups present at the 1- and/or 3β-positions may be removed by, for example, conventional methods such as are well documented in the literature. Thus esterifying acyl groups may be removed by basic hydrolysis, e.g. using an alkali metal alkoxide in an alkanol. Etherifying groups such as silyl groups may be removed by acid hydrolysis or treatment with a fluoride salt, e.g. a tetraalkylammonium fluoride. The use of such acid-labile but base-stable protecting groups may be of advantage when reactions involving strongly basic conditions are employed, e.g. in steps (C) and (D) above. Removal of such protecting groups will typically be performed as a final stage of a preparative sequence.

It will be appreciated that starting materials for step (B) above include 1α-hydroxy-20-oxo-cholecalciferol and its O-protected derivatives, which are known compounds. Such compounds may be converted to corresponding compounds (I) in which $R^1$ and $R^2$ together denote an oxo group, i.e. useful starting materials for step (C) above, e.g. by oxidation using techniques analogous to those for Barton/Gardner hydroxylation, the normally air-sensitive triene system of the compounds proving surprisingly stable under such oxidative conditions. Such 17-ones of formula (I) where $R^1$ and $R^2$ together denote an oxo group are themselves novel and, together with the above-described method for their preparation, represent further features of the invention. 1-Desoxy analogues of such 17-ones may similarly be prepared and subsequently 1-hydroxylated, e.g. by oxidation using an appropriate selenium compound as described in (A) above to effect 1-hydroxylation.

The following non-limitative Examples serve to illustrate the invention. All temperatures are in ° C.

PREPARATION 1

1α,3β-Bis-triisopropylsilyloxy-17-oxo-9,10-secoandrosta-5(E),7,10(19)-triene [5,6-trans analogue of compound (I) where $R^1+R^2=O$, $R^3=R^4=(i-Pr)_3Si$]

Air was passed through a solution of 1α,3β-bis-triisopropylsilyloxy-20-oxo-5,6-transpregnacalciferol [5,6-trans analogue of compound (I) where $R^1=CH_3CO$, $R^2=H$, $R^3=R^4=(i-Pr)_3Si$] (620 mg) in t-butanol (10 ml) containing potassium t-butoxide (6 ml of a 1M solution in tetrahydrofuran) maintained at 0°. After 3 hours the flow of air was stopped, the reaction mixture was purged with argon for 20 minutes, heated under reflux for 20 minutes, diluted with ether and worked up to give the title compound (250 mg isolated by chromatography): UV (Et$_2$O) $\lambda_{max}$ 268, $\lambda_{min}$ 228 nm; IR (CDCl$_3$) 1630, 1730 cm$^{-3}$; NMR (CDCl$_3$) δ 0.7 (s, 18-H's), 3.9–4.6 (m, 1,3-H's), 4.6–5.0 (bs, 19-H's), 5.3–6.3 (ABq, 6,7-H's).

PREPARATION 2

3β-Triisopropylsilyloxy-17-oxo-9,10-secoandrosta-5 (E),7,10(19)-triene [1-desoxy-5,6-trans analogue of compound (I) where R$^1$+R$^2$=O, R$^3$=(i-Pr)$_3$Si]

Air was passed through a solution of 3β-triisopropylsilyloxy-20-oxo-5,6-transpregnacalciferol [1-desoxy-5,6-trans analogue of compound (I) where R$^1$=CH$_3$CO, R$^2$=H, R$^3$=(i-Pr)$_3$Si] (460 mg) in t-butanol (10 ml) containing potassium t-butoxide (2.5 ml of a 1M solution in tetrahydrofuran) maintained at 0°. Further portions of potassium butoxide (3×2.5 ml of a 1M solution in tetrahydrofuran) were added at half hour intervals, whereafter the flow of air was stopped, the reaction mixture was purged with argon for 30 minutes, diluted with ether and worked up to give the title compound (190 mg isolated by chromatography): IR (CDCl$_3$) 1610, 1720 cm$^{-1}$.

This compound can be converted to the product of Preparation 1 by oxidation as described in GB-A-2038834 and appropriate silylation of the 1α-hydroxy compound so obtained.

PREPARATION 3

1α,3β-Bis-triisopropylsilyloxy-17α-hydroperoxy-20-oxo-9,10-secopregna-5(E),7,10(19)-triene [5,6-trans analogue of compound (I) where R$^1$=CH$_3$CO, R$^2$=OOH, R$^3$=R$^4$=(i-Pr)$_3$Si]

Air was passed through a solution of 1α,3β-bis-triisopropylsilyloxy-20-oxo-5,6-transpregnacalciferol [5,6-trans analogue of compound (I) where R$^1$=CH$_3$CO, R$^2$=H, R$^3$=R$^4$=(i-Pr)$_3$Si] (490 mg) in t-butanol (7.5 ml) containing potassium t-butoxide (4 ml of a 1M solution in tetrahydrofuran) maintained at 0°. After 2.5 hours the flow of air was stopped, the reaction mixture was purged with argon for 20 minutes, diluted with ether and worked up to give the title compound (250 mg isolated by chromatography): IR (CDCl$_3$) 3600–3100, 1620 cm$^{-1}$.

This compound can be converted to the product of Preparation 1 by heating in the presence of base, e.g. an alkali metal alkoxide such as potassium t-butoxide.

EXAMPLE 1 a) 1α,3β-Bis-triisopropylsilyloxy-17α-hydroxy-20-oxo-9,10-secopregna-5(E),7,10(19)-triene [5,6-trans analogue of compound (I) where R$^1$=CH$_3$CO, R$^2$=OH, R$^3$=R$^4$=(i-Pr)$_3$Si]

Air was passed through a solution of 1α,3β-bis-triisopropylsilyloxy-20-oxo-5,6-transpregnacalciferol [5,6-trans analogue of compound (I) where R$^1$=CH$_3$CO, R$^2$=H, R$^3$=R$^4$=(i-Pr)$_3$Si] (440 mg) in a mixture of tetrahydrofuran (2 ml), t-butanol (0.7 ml) and N,N-dimethylformamide (2 ml) containing triethylphosphite (0.7 ml) and potassium t-butoxide (2 ml of a 1M solution in tetrahydrofuran) maintained at −20°. After 30 minutes the reaction was diluted with ether and worked up to give the title compound (350 mg isolated by chromatography): WV (Et$_2$O) $\lambda_{max}$ 268, $\lambda_{min}$ 228 nm; IR (CDCl$_3$) 3620–3300, 1690, 1615 cm$^{-1}$; NMR (CDCl$_3$) δ 0.6 (s, 18-H's), 2.22 (s, 21-H's), 3.8–4.7 (m, 1,3-H's), 4.7–5.0 (bs, 19-H's), 5.5–6.5 (ABq, 6,7-H's).

Desilyation of this product (66 mg) using tetrabutylammonium fluoride in tetrahydrofuran afforded 1α,3β,17α-trihydroxy-20-oxo-9,10-secopregna-5(E),7,10(19)-triene [5,6-trans analogue of compound (I) where R$^1$=CH$_3$CO, R$^2$=OH, R$^3$=R$^4$=H] (28 mg): UV (EtOH) $\lambda_{max}$ 270, $\lambda_{min}$ 228 nm; IR (CDCl$_3$) 3620–3200, 1680, 1610 cm$^{-1}$; NMR (CDCl$_3$) δ 0.62 (s, 18-H's), 2.25 (s, 21-H's), 3.8–4.6 (m, 1,3-H's), 4.7, 5.0 (each s, 19-H's), 5.6–6.7 (ABq, 6,7-H's).

b) 1α,3β-Bis-triisopropylsilyloxy-17α-hydroxy-20-oxo-9,10-secopregna-5(Z),7,10(19)-triene [compound (I) where R$^1$=CH$_3$CO, R$^2$=OH, R$^3$=R$^4$=(i-Pr)$_3$Si]

The bis-silyl ether from (a) above (60 mg) in benzene (10 ml) containing phenazine (36 mg) was photoisomerised by UV irradiation (1 hour) to afford the title compound (50 mg isolated by chromatography): UV (Et$_2$O) $\lambda_{max}$ 262, $\lambda_{min}$ 225 nm; IR (CDCl$_3$) 3620–3340, 1695, 1630 cm$^{-1}$; NMR (CDCl$_3$) δ 0.56 (s, 18-H's), 2.23 (s, 21-H's), 4.0–4.7 (m, 1,3-H's), 4.7, 5.4 (each s, 19-H's), 5.8–6.5 (ABq, 6,7-H's).

Desilyation of this product (50 mg) using tetrabutylammonium fluoride in tetrahydrofuran afforded 1α,3β,17α-trihydroxy-20-oxo-9,10-secopregna-5(Z),7,10(19)-triene [compound (I) where R$^1$=CH$_3$CO, R$^2$=OH, R$^3$=R$^4$=H] (21 mg): UV (EtOH) $\lambda_{max}$ 262, $\lambda_{min}$ 226 nm; IR (CDCl$_3$) 3640–3300, 1695, 1630 cm$^{-1}$; NMR (CDCl$_3$) δ 0.57 (s, 18-H's), 2.18 (s, 21-H's), 3.7–4.6 (m, 1,3-H's), 4.7, 5.3 (each s, 19-H's), 5.8–6.4 (ABq, 6,7-H's).

EXAMPLE 2 a) 17α-Hydroxy-20-oxo-3β-triisopropylsilyloxy-9,10-secopregna-5(E),7,10(19)-triene [1-desoxy-5,6-trans analogue of compound (I) where R$^1$=CH$_3$CO, R$^2$=OH, R$^3$=(i-Pr)$_3$Si]

Air was passed through a solution of 20-oxo-3β-triisopropylsilyloxy-5,6-transpregnacalciferol [1-desoxy-5,6-trans analogue of compound (I) where R$^1$=CH$_3$CO, R$^2$=H, R$^3$=(i-Pr)$_3$Si] (130 mg) in a mixture of tetrahydrofuran (0.75 ml), t-butanol (0.25 ml) and N,N-dimethylformamide (0.75 ml) containing triethylphosphite (0.1 ml) and potassium t-butoxide (0.75 ml of a 1M solution in tetrahydrofuran) maintained at −20°. After 1 hour the reaction was diluted with ether and worked up to give the title compound (115 mg isolated by chromatography): UV (Et$_2$O) $\lambda_{max}$ 270, $\lambda_{min}$ 229 nm; IR (CDCl$_3$) 3620–3300, 1690, 1615 cm$^{-1}$; NMR (CDCl$_3$) δ 0.6 (s, 18-H's), 2.22 (s, 21-H's), 3.3–4.1 (m, 3-H), 4.4, 4.9 (each s, 19-H's), 5.5–6.5 (ABq, 6,7-H's).

Desilyation of this product (40 mg) using tetrabutylammonium fluoride in tetrahydrofuran afforded 3β,17α-dihydroxy-20-oxo-9,10-secopregna-5(E),7,10(19)-triene [1-desoxy-5,6-trans analogue of compound (I) where R$^1$=CH$_3$CO, R$^2$=OH, R$^3$=H] (28 mg): UV (EtOH) $\lambda_{max}$ 271, $\lambda_{min}$ 229 nm; IR (CDCl$_3$) 3640–3200, 1690, 1620 cm$^{-1}$; NMR (CDCl$_3$) δ 0.62 (s, 18-H's), 2.27 (s, 21-H's), 3.4–4.1 (m, 3-H), 4.5, 5.0 (each s, 19-H's), 5.6–6.6 (ABq, 6,7-H's).

b) 17α-Hydroxy-20-oxo-3β-triisopropylsilyloxy-9,10-secopregna-5(Z),7,10 (19)-triene [1-desoxy analogue of compound (I) where R$^1$=CH$_3$CO, R$^2$=OH, R$^3$=(i-Pr)$_3$Si]

The silyl ether from (a) above (75 mg) in benzene (16 ml) containing phenazine (57 mg) was photoisomerised by UV irradiation (1 hour) to afford the title compound (55 mg isolated by chromatography): WV (Et$_2$O) $\lambda_{max}$ 263, $\lambda_{min}$ 226 nm; IR (CDCl$_3$) 3620–3300, 1695, 1630 cm$^{-1}$; NMR (CDCl$_3$) δ 0.6 (s, 18-H's), 2.23 (s, 21-H's), 3.5–4.1 (m, 3-H), 4.5, 5.0 (each s, 19-H's), 5.6–6.2 (ABq, 6,7-H's).

Desilylation of this product (55 mg) using tetrabutylammonium fluoride in tetrahydrofuran afforded 3β,17α-dihydroxy-20-oxo-9,10-secopregna-5(Z),7,10(19)-triene [1-desoxy analogue of compound (I) where R$^1$=CH$_3$CO, R$^2$=OH, R$^3$=H]: UV (EtOH) $\lambda_{max}$ 262, $\lambda_{min}$ 225 nm; IR (CDCl$_3$) 3640–3200, 1695 cm$^{-1}$; NMR (CDCl$_3$) δ 0.6 (s, 18-H's), 2.23 (s, 21-H's), 3.5–4.1 (m, 3-H), 4.5, 5.1 (each s, 19-H's), 5.6–6.2 (ABq, 6,7-H's).

The 1-desoxy compounds produced according to this Example may be converted to 1α-hydroxy compounds according to the invention by oxidation as described in GB-A-2038834.

EXAMPLE 3 a) 1α,3β-Bis-triisopropylsilyloxy-17α-ethynyl-17β-hydroxy-9,10-secoandrosta-5(E),7,10(19)-triene [5, 6-trans analogue of compound (1) where R$^1$=OH, R$^2$=CH≡C, R$^3$=R$^4$=(i-Pr)$_3$Si]

A solution of 1α,3β-bis-triisopropylsilyloxy-17-oxo-9,10-secoandrosta-5(E),7,10(19)-triene from Preparation 1 (115 mg) and lithium acetylide ethylenediamine complex (184 mg) in dioxan (3 ml) was stirred at room temperature for 4 hours. The reaction mixture was then quenched with ice, diluted with ether and worked up. Chromatography afforded unreacted starting material (36 mg) and the title compound (35 mg): UV (Et$_2$O) $\lambda_{max}$ 268, $\lambda_{min}$ 226 nm; IR (CDCl$_3$) 3600, 3310, 1620 cm$^{-1}$; NMR (CDCl$_3$) δ 0.7 (s, 18-H's), 2.53 (s, ≡CH), 3.9–4.7 (m, 1,3-H's), 4.7–5.1 (bs, 19-H's), 5.5–6.5 (ABq, 6,7-H's).

b) 1α,3β-Bis-triisopropylsilyloxy-17α-ethynyl-17β-hydroxy-9,10-secoandrosta-5(Z),7,10(19)-triene [compound (I) where R$^1$=OH, R$^2$=CH≡C, R$^3$=R$^4$= (i-Pr)$_3$Si]

The product from (a) above (50 mg) in benzene (8 ml) containing phenazine (28 mg) was photoisomerised by UV irradiation (40 minutes) to afford the title compound (40 mg isolated by chromatography): UV (Et$_2$O) $\lambda_{max}$ 259, $\lambda_{min}$ 224 nm.

c) 1α,3β,17β-Trihydroxy-17α-ethynyl-9,10-secoandrosta-5(Z),7,10(19)-triene [compound (I) where R$^1$=OH, R$^2$=CH≡C, R$^3$=R$^4$=H]

The product from (b) above (40 mg) was desilylated by treatment with tetrabutylammonium fluoride (0.4 ml) in tetrahydrofuran (0.4 ml) for 3 hours at room temperature and the title compound (18 mg) was isolated by chromatography: UV (Et$_2$O) $\lambda_{max}$ 261, $\lambda_{min}$ 226 nm; IR (CDCl$_3$) 3600–3320, 3300, 1630 cm$^{-1}$; NMR (CDCl$_3$) δ 0.7 (s, 18-H's), 2.53 (s, ≡CH), 3.9–4.6 (m, 1,3-H's), 4.8, 5.4 (each s, 19-H's), 5.7–6.5 (ABq, 6,7-H's).

EXAMPLE 4 a) 1α,3β-Bis-triisopropylsilyloxy-17α-ethynyl-17β-methoxy-9,10-secoandrosta-5(E),7,10(19)-triene [5, 6-trans analogue of compound (I) where R$^1$=OCH$_3$, R$^2$=CH≡C, R$^3$=R$^4$=(i-Pr)$_3$Si]

Potassium hydride (200 μl of a 35% dispersion in mineral oil) was added dropwise to a solution of the product from Example 3(a) above (190 mg) in tetrahydrofuran (4 ml) containing 18-crown-6 (75 mg) and methyl iodide (200 μl) and maintained at −10°. After 40 minutes the reaction mixture was quenched with ice and worked up to give the title compound (185 mg purified by chromatography): UV (Et$_2$O) $\lambda_{max}$ 267, $\lambda_{min}$ 227 nm; IR (CCl$_4$) 3300, 1620 cm$^{-1}$; NMR (CCl$_4$) δ 0.63 (s, 18-H's), 2.43 (s, ≡CH), 3.3 (s, OMe-H's), 4.0–4.7 (m, 1,3-H's), 4.7–5.0 (bs, 19-H's), 5.5–6.6 (ABq, 6,7-H's).

b) 1α,3β-Bis-triisopropylsilyloxy-17α-ethynyl-17β-methoxy-9,10-secoandrosta-5(Z),7,10(19) -triene [compound (I) where R$^1$=OCH$_3$, R$^2$=CH≡C, R$^3$= R$^4$=(i-Pr)$_3$Si]

The product from (a) above (185 mg) in benzene (28 ml) containing phenazine (102 mg) was photoisomerised by UV irradiation (1.4 hours) to afford the title compound (165 mg purified by chromatography): UV (Et$_2$O) $\lambda_{max}$ 260, $\lambda_{min}$ 225 nm; IR (CCl$_4$) 3300, 1630 cm$^{-1}$; NMR (CCl$_4$) δ 0.63 (s, 18-H's), 2.4 (s, ≡CH), 3.23 (s, OMe-H's), 4.0–4.7 (m, 1,3-H's), 4.7, 5.3 (each s, 19-H's), 5.8–6.3 (ABq, 6,7-H's).

c) 1α,3β-Dihydroxy-17α-ethynyl-17β-methoxy-9, 10-secoandrosta-5(Z),7,10(19)-triene [compound (I) where R$^1$=OCH$_3$, R$^2$=CH≡C, R$^3$=R$^4$=H]

The product from (b) above (165 mg) was desilylated by treatment with tetrabutylammonium fluoride (1.5 ml) in tetrahydrofuran (1.5 ml) for 3 hours at room temperature and the title compound (70 mg) was isolated by chromatography): UV (Et$_2$O) $\lambda_{max}$ 261, $\lambda_{min}$ 225 nm; IR (CDCl$_3$) 3620–3200, 3290, 1620 cm$^{-1}$; NMR (CDCl$_3$) δ 0.7 (s, 18-H's), 2.27 (s, ≡CH), 3.35 (s, OMe-H's), 3.7–4.7 (m, 1,3-H's), 4.8, 5.4 (each s, 19-H's), 5.7–6.5 (ABq, 6,7-H's).

EXAMPLE 5 a) 1α,3β-Bis-triisopropylsilyloxy-20-ethynyl-20-hydroxy-9,10-secopregna-5(E),7,10(19)-triene [5,6-trans analogue of compound (I) where R$^1$=CH$_3$C (OH)(C≡CH), R$^2$=H, R$^3$=R$^4$=(i-Pr)$_3$Si]

A solution of 1α,3β-bis-triisopropylsilyloxy-20-oxo-5,6-transpregnacalciferol [5,6-trans analogue of compound (I) where R$^1$=CH$_3$CO, R$^2$=H, R$^3$=R$^4$=(i-Pr)$_3$Si] (321 mg) and lithium acetylide ethylenediamine complex (230 mg) in dioxan (10 ml) was stirred at room temperature for 1 hour. The reaction mixture was then quenched with ice, diluted with ether and worked up. Chromatography afforded unreacted starting material (50 mg) and the title compound (245 mg): UV (Et$_2$O) $\lambda_{max}$ 268, $\lambda_{min}$ 229 nm; IR (CDCl$_3$) 3580, 3300, 1615 cm$^{-1}$; NMR (CDCl$_3$) δ 0.8 (s, 18-H's), 2.33 (s, ≡CH), 3.8–4.7 (m, 1,3-H's), 4.7–5.0 (bs, 19-H's), 5.4–6.4 (ABq, 6,7-H's).

b) 1α,3β-Bis-triisopropylsilyloxy-20-ethynyl-20-hydroxy-9,10-secopregna-5(Z),7,10(19)-triene [compound (I) where R$^1$=CH$_3$C(OH)(C≡CH), R$^2$= H, R$^3$=R$^4$=(i-Pr)$_3$Si]

The product from (a) above (120 mg) in benzene (18 ml) containing phenazine (65 mg) was photoisomerised by UV irradiation (1.75 hours) to afford the title compound (100 mg purified by chromatography): UV (Et$_2$O) $\lambda_{max}$ 263, $\lambda_{min}$ 229 nm; IR (CDCl$_3$) 3600, 3300, 1610 cm$^{-1}$; NMR (CDCl$_3$) δ 0.8 (s, 18-H's), 3.9–4.6 (m, 1,3-H's), 4.6, 5.3 (each s, 19-H's), 5.8–6.3 (ABq, 6,7-H's).

c) 20-Ethynyl-1α,3β,20-trihydroxy-9,10-secopregna-5(Z),7,10 (19)-triene [compound (I) where R$^1$=C$_3$C(OH)(C≡CH), R$^2$=R$^3$=R$^4$=H]

The product from (b) above (100 mg) was desilylated by treatment with tetrabutylammonium fluoride (1 ml) in tetrahydrofuran (1 ml) for 4 hours at room temperature to afford the title compound (40 mg isolated by chromatography): UV (EtOH) $\lambda_{max}$ 262, $\lambda_{min}$ 225 nm; IR (CDCl$_3$) 3620–3320, 3300, 1600 cm$^{-1}$; NMR (CDCl$_3$) δ 0.83 (s, 18-H's), 1.47 (s, 21-H's), 2.56 (s, ≡CH), 3.9–4.8 (m, 1,3-H's), 4.8, 5.4 (each s, 19-H's), 5.8–6.6 (ABq, 6,7-H's).

EXAMPLE 6 a) 1α,3β-Bis-triisopropylsilyloxy-20-ethynyl-20-methoxy-9,10-secopregna-5(E),7,10(19)-triene [5,6-trans analogue of compound (I) where R$^1$=CH$_3$C(OCH$_3$)(C≡CH), R$^2$=H, R$^3$=R$^4$=(i-Pr)$_3$Si]

Potassium hydride (100 μl of a 35% dispersion in mineral oil) was added dropwise to a solution of the product from Example 5(a) above (120 mg) in tetrahydrofuran (3 ml) containing 18-crown-6 (50 mg) and methyl iodide (100 μl) and maintained at −10°. After 40 minutes the reaction mixture was quenched with ice and worked up to give the title compound (120 mg purified by chromatography): UV (Et$_2$O) $\lambda_{max}$ 268, $\lambda_{min}$ 228 nm; IR (CDCl$_3$) 3280, 1615 cm$^{-1}$; NMR (CDCl$_3$) δ 0.78 (s, 18-H's), 1.37 (s, 21-H's), 2.45 (s, ≡CH), 3.3 (s, OMe-H's), 4.0–4.8 (m, 1,3-H's), 4.8–5.1 (bs, 19-H's), 5.5–6.6 (ABq, 6,7-H's).

b) 1α,3β-Bis-triisopropylsilyloxy-20-ethynyl-20-=methoxy-9,10-secopregna-5(Z),7,10(19)-triene [compound (I) where R$^1$=CH$_3$C(OCH$_3$)(C≡CH), R$^2$=H, R$^3$=R$^4$=(i-Pr)$_3$Si]

The product from (a) above (120 mg) in benzene (18 ml) containing phenazine (65 mg) was photoisomerised by UV irradiation (2 hours) to afford the title compound (100 mg purified by chromatography): UV (Et$_2$O) $\lambda_{max}$ 262, $\lambda_{min}$ 227 nm; IR (CDCl$_3$) 3300, 1630 cm$^{-1}$; NMR (CDCl$_3$) δ 0.73 (s, 18-H's), 1.37 (s, 21-H's), 2.43 (s, ≡CH), 3.27 (s, OMe-H's), 3.9–4.6 (m, 1,3-H's), 4.6, 5.3 (each s, 19-H's), 5.8–6.3 (ABq, 6,7-H's).

c) 1α,3β-Dihydroxy-20-ethynyl-20-methoxy-9,10-secopregna-5(Z),7,10(19)-triene [compound (I) where R$^1$=CH$_3$C(OCH$_3$)(C≡CH), R$^2$=R$^3$=$^4$=H]

The product from (b) above (100 mg) was desilylated by treatment with tetrabutylammonium fluoride (0.9 ml) in tetrahydrofuran (0.9 ml) for 3 hours at room temperature to afford the title compound (48 mg isolated by chromatography): UV (EtOH) $\lambda_{max}$ 262, $\lambda_{min}$ 225 nm; IR (CDCl$_3$) 3620–3320, 3300, 1630 cm$^{-1}$; NMR (CDCl$_3$) δ 0.73 (s, 18-H's), 1.38 (s, 21-H's), 2.63 (s, =CH), 3.27 (s, OMe-H's), 3.8–4.6 (m, 1,3-H's), 4.7, 5.4 (each s, 19-H's), 5.6–6.6 (ABq, 6,7-H's).

EXAMPLE 7 a) 1α,3β-Bis-triisopropylsilyloxy-20-propynyl-20-trimethylsilyloxy-9,10-secopregna-5(E),7,10(19)-triene [5,6-trans analogue of compound (I) where R$^1$=CH$_3$C(OSiMe$_3$)(C≡CCH$_3$), R$^2$=H, R$^3$=R$^4$=(i-Pr)$_3$Si]

A solution of 1α,3β-bis-triisopropylsilyloxy-20-oxo-5,6-transpregnacalciferol [5,6-trans analogue of compound (I) where R$^1$=CH$_3$CO, R$^2$=H, R$^3$=R$^4$=(i-Pr)$_3$Si] (525 mg) and 1-trimethylsilylpropyne (242 mg) in tetrahydrofuran (2 ml) was treated at −15° with tetrabutylammonium fluoride (50 mg, dried at 95° and <0.5 mm for 6 hours) in tetrahydrofuran (1 ml), stirred for 1 hour at 0°, then treated with further 1-trimethylsilylpropyne (242 mg) and tetrabutylammonium fluoride (50 mg, dried as above) in tetrahydrofuran (1 ml) and allowed to warm to room temperature. After a further hour ether was added and the reaction mixture was worked up. The title compound (225 mg) was isolated by chromatography on silica gel, eluting with 10% toluene in hexane: UV (Et$_2$O) $\lambda_{max}$ 268, $\lambda_{min}$ 228 nm; IR (CCl$_4$) 1620 cm$^{-1}$; NMR (CCl$_4$) δ 0.13 (s, SiMe$_3$-H's), 0.7 (s, 18-H's), 1.33 (s, 21-H's), 1.76 (s, ≡CCH$_3$), 3.8–4.7 (m, 1,3-H's), 4.7–5.4 (bs, 19-H's), 5.4–6.5 (ABq, 6,7-H's).

Further elution with 1% ethyl acetate in hexane afforded material (265 mg) believed to be an analogue of the title compound with one of the ring-A triisopropylsilyl groups replaced by trimethylsilyl: UV (Et$_2$O) $\lambda_{max}$ 270, $\lambda_{min}$ 229 nm; IR (CCl$_4$) 1615 cm$^{-1}$; NMR (CCl$_4$) δ 0.13 (s, SiMe$_3$-H's), 0.7 (s, 18-H's), 1.33 (s, 21-H's), 1.73 (s, ≡CCH$_3$), 3.8–4.6 (m, 1,3-H's), 4.6–5.0 (d, 19-H's), 5.4–6.4 (ABq, 6,7-H's)

b) 1α,3β-Bis-triisopropylsilyloxy-20-propynyl-20-trimethylsilyloxy-9,10-secopregna-5(Z),7,10(19)-triene [compound (I) where R$^1$=CH$_3$C(OSiMe$_3$)(C≡CH$_3$), R$^2$=H, R$^3$=R$^4$=(i-Pr)$_3$Si]

The title compound from (a) above (225 mg) in benzene (30 ml) containing phenazine (108 mg) was photoisomerised by UV irradiation (1.5 hours—the solution was irradiated in two flasks) to afford the title compound (200 mg purified by chromatography): UV (Et$_2$O) $\lambda_{max}$ 262, $\lambda_{min}$ 226 nm; IR (CCl$_4$) 1630 cm$^{-1}$; NMR (CCl$_4$) δ 0.13 (s, SiMe$_3$-H's), 0.63 (s, 18-H's), 1.33 (s, 21-H's), 1.76 (s, ≡CCH$_3$), 3.8–4.6 (m, 1,3-H's), 4.6, 5.3 (each s, 19-H's), 5.6–6.3 (ABq, 6,7-H's).

c) 1α,3β,20-Trihydroxy-20-propynyl-9,10-secopregna-5(Z),7,10(19)-triene [compound (I) where R$^1$=CH$_3$C(OH)(C≡CCH$_3$), R$^2$=R$^3$=R$^4$=H]

The product from (b) above (200 mg) was desilylated by treatment with tetrabutylammonium fluoride (2.6 ml) in tetrahydrofuran (2.6 ml) for 3 hours at room temperature and the title compound (90 mg) was isolated by chromatography): UV (EtOH) $\lambda_{max}$ 263, $\lambda_{min}$ 225 nm; IR (CDCl$_3$) 3660–3100, 1620 cm$^{-1}$; NMR (CDCl$_3$) δ 0.8 (s, 18-H's), 1.43 (s, 21-H's,) 1.76 (s, ≡CCH$_3$), 3.8–4.7 (m, 1,3-H's), 4.8, 5.4 (each s, 19-H's), 5.7–6.5 (ABq, 6,7-H's).

EXAMPLE 8 a) 1α,3β-Bis-triisopropylsilyloxy-17α-(3-triisopropylsilyloxypropyn-1-yl)-17β-trimethylsilyloxy-9,10-secoandrosta-5(E),7,10(19)-triene [5,6-trans analogue of compound (1) where R$^1$=OSiMe$_3$, R$^2$=—C≡C—CH$_2$OSi(i-Pr)$_3$, R$^3$=R$^4$=(i-Pr)$_3$Si]

A solution of 1α,3β-bis-triisopropylsilyloxy-17-oxo-9,10-secoandrosta-5(E),7,10(19)-triene from Preparation 1 (350 mg) in tetrahydrofuran (1 ml) containing dried tetrabutylammonium fluoride (50 mg) was treated with 1-trimethylsilyl-3-triisopropylsilyloxypropyne (340 mg) according to the procedure of Example 7(a) to afford the title compound (260 mg, isolated by column chromatography): UV (Et$_2$O) $\lambda_{max}$ 268, $\lambda_{min}$ 227 nm; IR (CDCl$_3$) 1620 cm$^{-1}$; NMR (CDCl$_3$) δ 0.13 (s, SiMe$_3$-H's), 0.6 (s, 18-H's), 3.8–4.6 (m, 1,3-H's, ≡C—CH$_2$O—), 4.6–5.0 (bs, 19-H's), 5.3–6.3 (ABq, 6,7-H's).

b) 1α,3β-Bis-triisopropylsilyloxy-17α-(3-triisopropylsilyloxypropyn-1-yl)-17β-trimethylsilyloxy-9,10-secoandrosta-5(Z),7,10(19)-triene [compound (I) where R$^1$=OSiMe$_3$, R$^2$=—C≡C—CH$_2$OSi(i-Pr)$_3$, R$^3$=R$^4$=(i-Pr)$_3$Si]

The compound from (a) above (120 mg) in benzene containing phenazine (47 mg) was photoisomerised as in Example 7(b) to afford the title compound (85 mg, purified by chromatography): UV (Et$_2$O) $\lambda_{max}$ 261, $\lambda_{min}$ 224 nm; IR (CDCl$_3$) 1620 cm$^{-1}$; NMR (CDCl$_3$) δ 0.13 (s, SiMe$_3$-H's), 0.57 (s, 18-H's), 3.9–4.6 (m, 1,3-H's, ≡C—CH$_2$O—), 4.6–5.3 (2xbs, 19-H's), 5.5–6.3 (ABq, 6,7-H's).

c) 1α,3β,17β-Trihydroxy-17α-(3-hydroxypropyn-1-yl)-9,10-secoandrosta-5(Z),7,10(19)-triene [compound (I) where R$^1$=OH, R$^2$=—C≡C—CH$_2$OH, R$^3$=R$^4$=H]

The compound from (b) above (85 mg) in tetrahydrofuran (1.2 ml) was desilylated with tetrabutylammonium fluoride (1.2 ml) in tetrahydrofuran (1.2 ml) by the procedure of Example 7(c) to afford the title compound (21 mg, isolated by preparative thin layer chromatography): UV (EtOH) $\lambda_{max}$ 262, $\lambda_{min}$ 225 nm; NMR (CD$_3$OD) δ 0.63 (s, 18-H's), 3.3–4.4 (m, 1,3-H's, ≡C—CH$_2$O—), 4.4–5.4 (2xbs, 19-H's), 5.7–6.4 (ABq, 6,7-H's).

EXAMPLE 9 a) 1α,3β-Bis-triisopropylsilyloxy-20-(3-triisopropylsilyloxypropyn-1-yl)-20-trimethylsilyloxy-9,10-secopregna-5(E),7,10(19)-triene [6-trans analogue of compound (I) where R$^1$=—C(OSiMe$_3$)(C≡C,CH$_2$OSi(i-Pr)$_3$)CH$_3$, R$^2$=H, R$^3$=R$^4$=(i-Pr)$_3$Si]

A solution of 1α,3β-bis-triisopropylsilyloxy-20-oxo-5,6-transpregnacalciferol (575 mg) in tetrahydrofuran (3 ml) was treated with dried tetrabutylammonium fluoride (100 mg) and 1-trimethylsilyl-3-triisopropylsilyloxypropyne (2 portions, 575 mg and 256 mg) according to the procedure of Example 7(a) to give the title compound (315 mg, isolated by column chromatography): IR (CDCl$_3$) 1610 cm$^{-1}$; NMR (CDCl$_3$) δ 0.73 (s, 18-H's), 1.4 (s, 21-H's), 3.9–4.7 (m, 1,3-H's, ≡C—CH$_2$O—), 4.7–5.4 (bs, 19-H's), 5.3–6.6 (ABq, 6,7-H's).

b) 1α,3β-Bis-triisopropylsilyloxy-20-(3-triisopropylsilyloxypropyn-1-yl)-20-trimethylsilyloxy-9,10-secopregna-5(Z 7,10(19)-triene [compound (I) where R$^1$=—C(OSiMe$_3$)(C≡C,CH$_2$OSi (i-Pr)$_3$)CHR$_3$, R$^2$=H, R$^3$=R$^4$=(i-Pr)$_3$Si]

The compound from (a) above (315 mg) in benzene (17 ml) with phenazine (122 mg) was photoisomerised as in Example 7(b) to afford the title compound (225 mg, isolated by chromatography): UV $\lambda_{max}$ 261, $\lambda_{min}$ 225 nm; IR(CDCl$_3$) 1620 cm$^{-1}$; NMR (CDCl$_3$) δ 0.17 (s, SiMe$_3$-H's), 0.7 (s, 18-H's), 3.8–4.5 (m, 1,3-H's, ≡C—CH$_2$O—), 4.5–5.3 (2xbs, 19-H's), 5.5–6.4 (ABq, 6,7-H's).

c) 1α,3β,20-Trihydroxy-20-(3-hydroxypropyn-1-yl)-9,10-secopregna-5(Z),7,10(19)-triene [compound (I) where R$^1$=—C(OH)(C≡C,CH$_2$OH)CH$_3$, R$^2$=R$^3$=R$^4$=H]

The compound from (b) above (225 mg) in tetrahydrofuran (2.9 ml) was desilylated with tetrabutylammonium fluoride (2.9 ml) in tetrahydrofuran (2.9 ml) as in Example 7(c) to afford the title compound(45 mg, isolated by chromatography): UV (EtOH) $\lambda_{max}$ 261, $\lambda_{min}$ 225 nm; NMR (CDCl$_3$, CD$_3$OD) δ 0.73 (s, 18-H's), 1.4 (s, 21-H's), 3.7–4.5 (m, 1,3-H's, ≡C—CH$_2$O—), 4.6–5.3 (2xbs, 19-H's), 5.5–6.4 (ABq, 6,7-H's).

EXAMPLE 10 a) 1α,3β-Bis-triisopropylsilyloxy-20-propargyl-20-hydroxy-9,10-secopregna-5(E),7,10(19)-triene [5,6-trans analogue of compound (I) where R$^1$=C(OH)(CH$_2$,C≡CH)CH$_3$, R$^2$=H, R$^3$=R$^4$=(i-Pr)$_3$Si]

A solution of 1α,3β-bis-triisopropylsilyloxy-20-oxo-5,6-transpregnacalciferol (445 mg) in tetrahydrofuran (12 ml) was added dropwise at room temperature to a solution of "propargyl aluminum" [prepared by addition of a solution of propargyl bromide (769 mg of a 80% w/w solution in toluene) in ether (5 ml) to a mixture of aluminium powder (93 mg) and mercuric chloride in ether (1 ml), followed by heating under reflux for 5 hours]. The reaction mixture was stored at room temperature for 30 minutes, diluted with ether, treated with wet sodium sulphate and filtered, whereafter the filtrate was concentrated in vacuo. The product (100 mg, isolated by chromatography after storage in a freezer for 4 weeks) had UV (Et$_2$O) $\lambda_{max}$ 271, $\lambda_{min}$ 228 nm; IR(CDCl$_3$) 3700–3300, 3280, 1610 cm$^{-1}$; NMR (CDCl$_3$) δ 0.66 (s, 18-H's), 3.8–4.5 (m, 1,3-H's), 4.5–4.8 (bs, 19-H's), 5.2–6.3 (ABq, 6,7-H's).

b) 1α,3β-bis-triisopropylsilyloxy-20-propargyl-20-hydroxy-9,10-seco-pregna-5(Z),7,10(19)-triene [compound (I) where R$^1$=C(OH)(CH$_2$,C≡CH)CH$_3$, R$^2$=H, R$^3$=R$^4$=(i-Pr)$_3$Si]

The compound from (a) above (100 mg) in benzene (7 ml) with phenazine (53 mg) was photoisomerised as in Example 7(b) to afford the title compound (60 mg, isolated by chromatography): UV (Et$_2$O) $\lambda_{max}$ 262, $\lambda_{min}$ 225 nm; IR (CDCl$_3$) 3660–3200, 3300, 1600 cm$^{-1}$; NMR (CDCl$_3$) δ 0.6 (s, 18-H's), 1.36 (21-H's), 3.8–4.6 (m, 1,3-H's), 4.6–5.3 (2xbs, 19-H's), 5.5–6.4 (ABq, 6,7-H's).

c) 1α,3β,20-Trihydroxy-20-20-propargyl-9,10-secopregna-5(Z),7,10(19)-triene [compound (I) where R$^1$=C(OH),(CH$_2$,C≡CH)CH$_3$, R$^2$=R$^3$=R$^4$=H]

The compound from (b) above (60 mg) in tetrahydrofuran (0.6 ml) was desilylated with tetrabutylammonium fluoride (0.6 ml) in tetrahydrofuran (0.6 ml) as in Example 7(a) to afford the title compound (45 mg, isolated by chromatography): UV (EtOH) $\lambda_{max}$ 263, $\lambda_{min}$ 225 nm; IR (CDCl3) 3640–3200, 3300, 1620 cm$^{-1}$; NMR (CDCl$_3$) δ 0.66 (s, 18-His), 1.33 (21-H's), 3.6–4.4 (m, 1,3-H's), 4.6–5.2 (2xbs, 19-H's), 5.5–6.4 (ABq, 6,7-H's).

EXAMPLE 11 a) 1β,3β-Bis-triisopropylsilyloxy-20-propynyl-20-trimethylsilyloxy-9,10-secopregna-5(Z),7,10(19)-triene [5,6-trans analogue of compound (I) where R$^1$=—C(OSiMe$_3$)(C≡C,CH$_3$)CH$_3$, R$^2$=H, R$^3$=R$^4$=(i-Pr)$_3$Si]

A solution of 1β,3β-bis-triisopropylsilyloxy-20-oxo-5,6-transpregnacalciferol (419 mg) and 1-(trimethylsilyl)-propyne (145 mg) in tetrahydrofuran (2 ml) was twice treated at 0° with dried tetrabutylammonium fluoride (2x50 mg) in tetrahydrofuran (2x1 ml) according to the procedure of Example 7(a) to give the title compound (135 mg, isolated by chromatography): UV (Et$_2$O) $\lambda_{max}$ 265, $\lambda_{min}$ 227 nm; IR (CCl$_4$) 1620 cm$^{-1}$; NMR (CCl$_4$) δ 0.13 (s, SiMe$_3$-H's), 0.73 (s, 18-H's), 1.36 (s, 21-H's), 1.76 (s, ≡C—CH$_3$), 3.3–4.4 (m, 1,3-H's), 4.7–5.2 (bs, 19-H's), 5.4–6.5 (ABq, 6,7-H's). [The pregnacalciferol starting material was prepared from 1β,3β-bis-triisopropylsilyloxy vitamin D$_2$ by following the procedure of Claverly et al. (WO 90/09991), or by silylation of the minor 1β-OH product obtained by 1-hydroxylating 20-oxo-3β-triisopropylsilyloxy-5,6-transpregnacalciferol following the procedure of GB-A-2038834. 1β,3β-Bis-triisopropylsilyloxy vitamin D$_2$ was itself prepared by isolating and silylating the minor 1β-OH product obtained by 1-hydroxylating vitamin D$_2$ following the procedure of GB-A-2038834.]

b) 1β,3β-Bis-triisopropylsilyloxy-20-propynyl-20-trimethylsilyloxy-9,10-secopregna-5(Z),7,10(19)-triene [compound (I) where $R^1$=—C(OSiMe$_3$) (C≡C,CH$_3$)CH$_3$, $R^2$=H, $R^3$=$R^4$=(i-Pr)$_3$Si]

The compound from (a) above (135 mg) in benzene (18 ml) containing phenazine (65 mg) was photoisomerised as in Example 7(b) to give the title compound (130 mg, purified by chromatography): UV (Et$_2$O) $\lambda_{max}$ 257, $\lambda_{min}$ 225 nm; NMR (CCl$_4$) δ 0.13 (s, SiMe$_3$-H's), 0.7 (s, 18-H's), 1.36 (s, 21-H's), 1.76 (s, ≡C—CH$_3$), 3.4–4.3 (m, 1,3-H's), 4.6, 5.5 (each bs, 19-H's), 5.5–6.3 (ABq, 6,7-H's).

c) 1β,3β,20-Trihydroxy-20-propynyl-9,10-secopregna-5(Z),7,10(19)-triene [compound (I) where $R^1$=—C(OH)(C≡C,CH$_3$)CH$_3$, $R^2$=$R^3$=$R^4$=H]

The silyl ether from (b) above (130 mg) was desilylated with tetrabutylammonium fluoride (1.8 ml) in tetrahydrofuran (1.8 ml) as in Example 7(c) to give the title compound (60 mg, isolated by chromatography): TV (EtOH) $\lambda_{max}$ 261, $\lambda_{min}$ 224 nm; IR (CDCl$_3$) 3660–3100, 1620 cm$^{-1}$; NMR (CDCl$_3$) 0.77 (s, 18-H's), 1.4 (s, 21-H's), 1.77 (s, ≡C—CH$_3$), 3.4–4.5 (m, 1,3-H's), 4.8, 5.3 (each bs, 19-H's), 5.7–6.6 (ABq, 6,7-H's).

EXAMPLE 12 a) 1β,3βBis-triisopropylsilyloxy-20-ethynyl-20-hydroxy-9,10-secopregna-5(E),7,10(19)-triene [5,6-trans analogue of compound (I) where $R^1$=—C(OH)(C≡CH) CH$_3$, $R^2$=H, $R^3$=$R^4$=(i-Pr)$_3$Si]

A solution of 1β,3β-bis-triisopropylsilyloxy-20-oxo-5,6-transpregnacalciferol (420 mg) and lithium acetylide ethylenediamine complex (598 mg) in dioxan (7 ml) was treated as in Example 5(a) to give the title compound (210 mg, isolated by chromatography): UV (Et$_2$O) $\lambda_{max}$ 266, $\lambda_{min}$ 227 nm; IR (CCl$_4$) 3600–3200, 3000, 1615 cm$^{-1}$; NMR (CCl$_4$) δ 0.77 (s, 18-H's), 1.4 (s, 21-H's), 2.26 (s, ≡CH), 3.3–4.2 (m, 1,3-H's), 4.6–5.1 (bs, 19-H's), 5.4–6.4(ABq, 6, 7-H's).

b) 1β,3β-Bis-triisopropylsilyloxy-20-ethynyl-20-hydroxy-9,10-secopregna-5(Z),7,10(19)-triene [compound (I) where $R^1$=—C(OH) (C≡CH)C$_3$, $R^2$=H, $R^3$=$R^4$=(i-Pr)$_3$Si]

The ethynyl compound from (a) above (170 mg) in benzene (26 ml) containing phenazine (92 mg) was photoisomerised as in Example 7(b) by irradiation (2M hours) to afford the title compound (150 mg, purified by chromatography): UV (Et$_2$O) $\lambda_{max}$ 257, $\lambda_{min}$ 224 nm; IR (CCl$_4$) 3620–3200, 3300, 1630 cm; NMR (CCl$_4$) δ 0.77 (s, 18-H's), 1.43 (s, 21-H's), 2.3 (s, ≡C-H), 3.4–4.2 (m, 1,3-H's), 4.6, 5.1 (each bs, 19-H's), 5,6–6.2 (ABq, 6,7-H's).

c) 20-Ethynyl-1β,3β,20-trihydroxy-9,10-secopregna-5(Z),7,10(19)-triene [compound (I) where $R^1$=—C(OH) (C≡CH)CH$_3$, $R^2$=$R^3$=$R^4$=H]

The silyl ether from (b) above (150 mg) was desilylated as in Example 7(c) using tetrabutylammonium fluoride (1.5 ml) to give the title compound (68 mg, isolated by chromatography): UV (EtOH) $\lambda_{max}$ 260, $\lambda_{min}$ 224 nm; IR (CDCl$_3$) 3660–3100, 3280, 1620cm$^{-1}$; NMR (CDCl$_3$)δ 0.8 (s, 18-H's), 1.48 (s, 21-H's), 2.47 (s, ≡C-H), 3.7–4.5 (m, 1,3-H's), 4.7, 5.3 (each bs, 19-H's), 5.7–6.3 (ABq, 6,7-H's).

EXAMPLE 13 a) 1α,3β-Bis-triisopropylsilyloxy-20-oxo-9,10-secopregna-5(Z),7,10 (19)-triene [compound (I) where $R^1$=CH$_3$,CO—, $R^2$=H, $R^3$=$R^4$=(i-Pr$_3$) Si]

The compound 1β,3β-bis-triisopropylsilyloxy-20-oxo-9,10-secopregna-5(E),7,10(19)-triene prepared according to Claverly et al. (WO 90/09991) (170 mg) in benzene (27 ml) with phenazine (89 mg) was photoisomerised as in Example 7(b) to afford the title compound (130 mg, isolated by chromatography): UV (Et$_2$O) $\lambda_{max}$ 261, $\lambda_{min}$ 226 nm; IR (CDCl$_3$) 1690, 1620 cm$^{-1}$; NMR (CDCl$_3$) δ 0.46 (s, 18-Hs), 2.03 (21-H's), 3.7–4.6 (m, 1,3-H's), 4.6–5.2 (2xbs, 19-H's), 5.5–6.4 (ABq, 6,7-H's).

b) 1α,3β-Dihydroxy-20-oxo-9,10-secopregna-5(Z), 7,10(19)-triene [compound (I) where $R^1$=CH$_3$, CO—, $R^2$=$R^3$=$R^4$=H]

The compound from (a) above (130 mg) in tetrahydrofuran (1.2 ml) was desilylated with tetrabutylammonium fluoride (1.2 ml) in tetrahydrofuran (1.2 ml) as in Example 7(c) to afford the title compound (53 mg, isolated by chromatography): UV (EtOH) $\lambda_{max}$ 263, $\lambda_{min}$ 226 nm; IR (CDCl$_3$) 3660–3200, 3300, 1700, 1640 cm$^{-1}$; NMR (CDCl$_3$) δ 0.5 (s, 18-H's), 2.07 (21-H's), 3.7–4.4 (m, 1,3-H's), 4.7–5.4 (2xbs, 19-H's), 5,6–6.6 (ABq, 6,7-H's).

What is claimed is:

1. Compounds of formula (I)

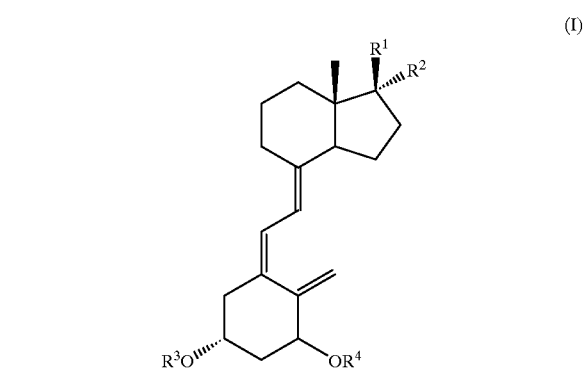

(I)

or the corresponding 5,6-trans isomers thereof, wherein:

$R^1$ denotes a hydroxyl, protected hydroxyl or $C_{1-6}$ alkoxy group and $R^2$ denotes a $C_{2-6}$ alkynyl group optionally substituted by a hydroxyl, protected hydroxyl or $C_{1-6}$ alkoxy group;

and $R^3$ and $R^4$ are each selected from the group consisting of hydrogen atoms and O-protecting groups.

2. A compound as claimed in claim 1 wherein:

$R^1$ denotes a hydroxyl, tri($C_{1-6}$alkyl)silyloxy or methoxy group and $R^2$ denotes a $C_{2-6}$alkynyl group optionally substituted by a hydroxyl, tri($C_{1-6}$ alkyl)silyloxy or methoxy group.

3. A compound as claimed in claim 1 wherein $R^2$ represents a $C_{2-6}$ alk-1-yn-1-yl group and the group —$OR^4$ is in the α-configuration.

4. The compounds selected from the group consisting of:

1α,3β,17β-trihydroxy-17α-ethynyl-9,10-secoandrosta-5 (Z),7,10(19)-triene; and

1α,3β-dihydroxy-17α-ethynyl-17β-methoxy-9,10-secoandrosta-5(Z),7,10(19)-triene.

5. A compound which is:

1α,3β, 17β-trihydroxy-17α-(3-hydroxypropyn-1-yl)-9,10-secoandrosta-5(Z),7,10(19)-triene.

6. A pharmaceutical composition comprising a compound of formula (I)

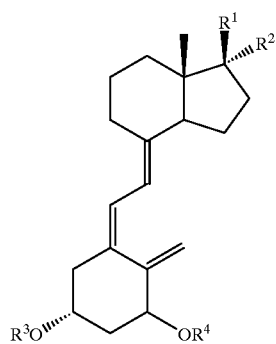
(I)

or a corresponding 5,6-trans isomer thereof, wherein:

$R^1$ denotes a hydroxyl, protected hydroxyl or $C_{1-6}$ alkoxy group and $R^2$ denotes a $C_{2-6}$ alkynyl group optionally substituted by a hydroxyl, protected hydroxyl or $C_{1-6}$ alkoxy group;

and $R^3$ and $R^4$ are each selected from hydrogen atoms and metabolically labile O-protecting groups;

in admixture with one or more physiologically acceptable carriers and/or excipients.

* * * * *